United States Patent [19]

Reed et al.

[11] Patent Number: 4,583,468
[45] Date of Patent: Apr. 22, 1986

[54] METHOD AND APPARATUS FOR COMBUSTION OF DIVERSE MATERIALS AND HEAT UTILIZATION

[75] Inventors: Leland M. Reed; William A. Reed, both of Cincinnati, Ohio; Walter C. Saeman, NE. Cleveland, Tenn.

[73] Assignee: PEDCo, Inc., Cincinnati, Ohio

[21] Appl. No.: 518,219

[22] Filed: Jul. 28, 1983

[51] Int. Cl.[4] ................................................ F23G 5/06
[52] U.S. Cl. ...................................... 110/246; 432/106; 432/111; 34/128
[58] Field of Search .............. 110/246; 432/106, 110, 432/111, 118, 105; 34/128

[56] References Cited

U.S. PATENT DOCUMENTS

| | | | |
|---|---|---|---|
| 2,468,871 | 5/1949 | Fomi | 432/111 |
| 3,413,937 | 12/1968 | Bojner et al. | 110/246 |
| 3,705,711 | 12/1972 | Seelandt et al. | 110/246 |
| 3,822,651 | 7/1974 | Harris et al. | 110/246 |
| 4,038,025 | 7/1977 | Kratochuil | 432/106 |
| 4,066,024 | 1/1978 | O'Connor | 110/246 |
| 4,274,342 | 6/1981 | Nider | 110/246 |
| 4,285,773 | 8/1981 | Taciuk | 34/128 |
| 4,395,958 | 8/1983 | Caffyn et al. | 110/246 |
| 4,427,376 | 1/1984 | Etnyre et al. | 432/111 |
| 4,437,418 | 3/1984 | Guillaume et al. | 110/246 |

Primary Examiner—Henry C. Yuen
Attorney, Agent, or Firm—Wood, Herron & Evans

[57] ABSTRACT

A method and apparatus is disclosed for combustion of diverse materials, particularly combustible solids, liquids or gases, such as sewage sludge, refuse, coal, refinery sludge, tar sands, coal shale, coal tailings and spent foundry sand. A rotary combustion apparatus is employed which consists of a cylindrical drum, or other similar regularly shaped chamber, with a substantially horizontal axis of rotation including an ignition zone, a principal combustion zone, a falling temperature zone and a spent solids removal zone. The apparatus further includes solids transport chutes for forward and backward circulation of solids, arranged for the transfer of solids to or from one or more points. Feedstock may also be heated by recycled hot solids. The method and apparatus employs direct solids-to-gas contact established by lifting and cascading combustible solids through a hot gas stream.

24 Claims, 6 Drawing Figures

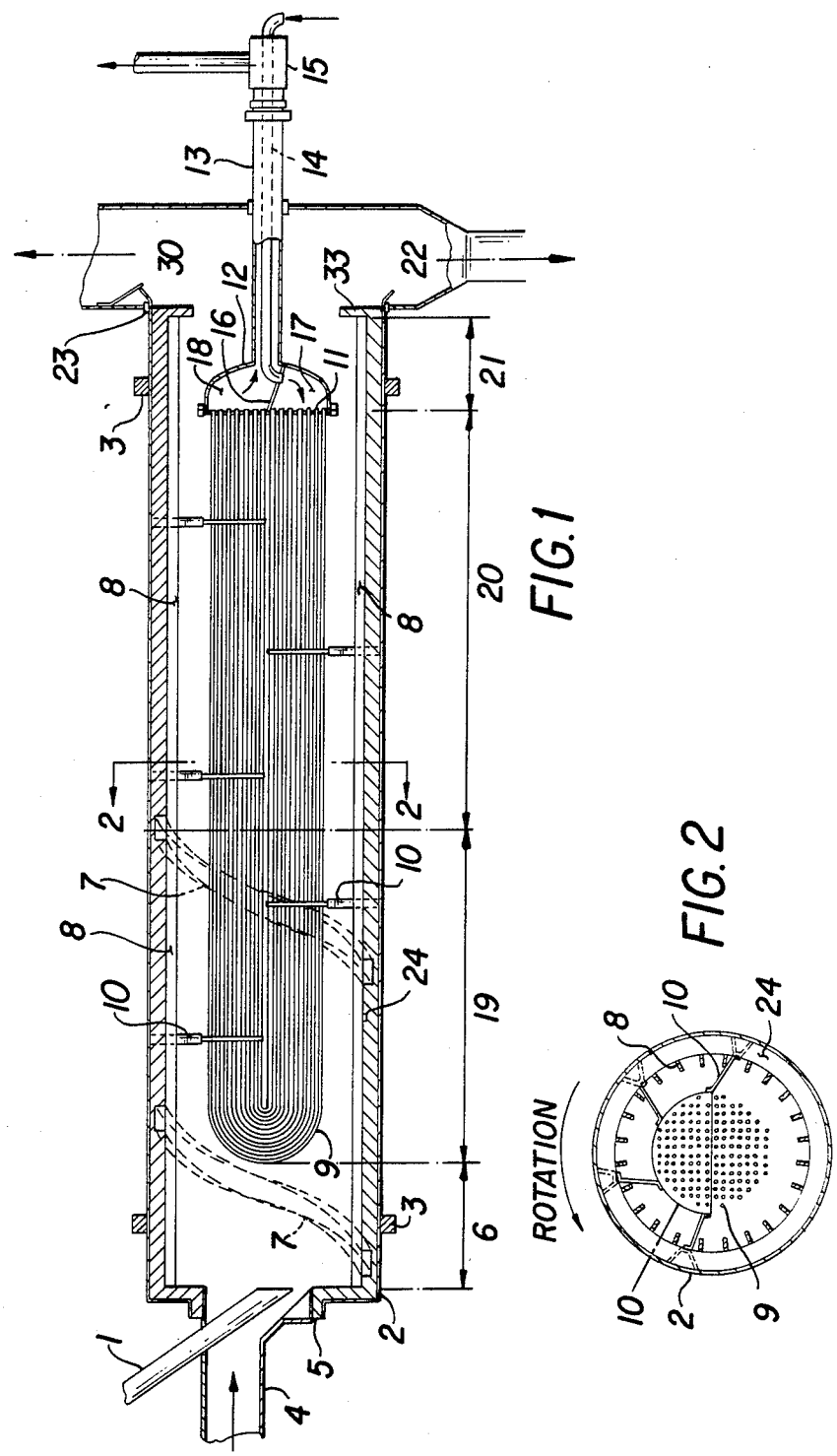

METHOD AND APPARATUS FOR COMBUSTION OF DIVERSE MATERIALS AND HEAT UTILIZATION

BACKGROUND OF THE INVENTION

Conventional solid fuel furnaces or combustion apparatus utilize one of four general methods for introducing and burning fuel. These methods are referred to as overfeed firing, underfeed firing, pulverized fuel burning, and fluidized bed combustion. Each of these techniques is very well known and typical examples of types of apparatus employing these techniques are discussed in "Steam Its Generation and Use" by Babcock and Wilcox, 37th Ed. (1963) and "Combustion Engineering" by Combustion Engineering, Inc., Revised Ed. (1966) Lib. of Congress Catalog No. 6623939. The overfeed firing method involves the introduction of fuel into a furnace over the fire in a uniform spreading action such as with a traveling-grate stoker. The overfeed firing method of combustion is relatively inefficient because of the difficulty in achieving complete and even combustion of the fuel and, furthermore, most sulfur-containing fuels require the addition of complex and expensive external scrubbing systems to the furnace. In the case of the underfeed firing method, fuel is introduced into a chamber where a series of pushers or rams move the fuel upward for spreading between air-admitting tuyeres and side-grates. As the fuel rises in the chamber, it is ignited by the heat from the burning fuel above and continues to burn as the incoming raw fuel forces the fuel bed upward. Underfeed firing has many of the same disadvantages as overfeed firing and, furthermore, the ash content must be critically controlled between 3 and 10% so as not to become a hindrance to proper combustion. In pulverized fuel combustion, the fuel is pulverized and then mixed with transport air for conveyance to the furnace where it is burned. Pulverized fuel burning has many drawbacks including the cost of pulverization and the production of large quantities of fly ash which may require the installation of particulate-removal equipment which also adds to the cost of the system. In fluidized bed combustion, the combustible materials are usually ground to a suitable size enabling their fluidization in a stream of high velocity air and combustion takes place in the fluidized bed. The fluidized bed method requires a significant amount of energy to maintain its fluidized state and the temperatures of operation are relatively low. Furthermore, in addition to the fly ash produced, a major disadvantage of this last technique is the incomplete combustion of fines which are swept out of the fluidized bed by the air stream and require either capture and reinjection or burn-out of the carbon in a separate bed.

Other problems are encountered in current state of the art methods of combustion and apparatus. For instance, where a fuel containing sulfur compounds is burned as is the case with coal, the sulfur oxides produced are particularly hazardous to the environment because, upon release into the atmosphere, they combine with water to produce acidic materials, namely, sulfurous and sulfuric acid. When these acids are dissolved in rain, they produce what is commonly referred to as "acid rain" which may cause environmental damage. Sulfur oxides may be removed from the flue gases and most of the methods available involve the treatment of the gases outside the furnace by chemically acceptable means, such as caustic scrubbing or reaction with lime, limestone or dolomite slurries. These methods of sulfur oxide removal require expensive, corrosion-resistive equipment which adds greatly to the cost of the system and requires inconvenient and expensive slurry disposal systems which are environmentally objectionable.

In pulverized fuel burning and fluidized bed combustion systems, powdered or crushed additives such as limestone or dolomite may be added to the fuel for reaction with the sulfur oxides within the furnace. This method is inefficient in systems which burn pulverized fuel because of the relatively high furnace temperatures employed. In fluidized bed combustion, where the temperature is favorable, a substantial part of the sulfur oxides fails to react with the additive and may escape to the atmosphere unless an excess of limestone or dolomite is used. A number of other problems are encountered by employing limestone or dolomite additives in a fluidized bed. For instance, the size of the additive must be controlled such that it is carried out of the system with the fly ash but this does not usually provide optimum reaction time and conditions, or the additive must be of such size as the coal, in which case it becomes coated with calcium sulfate reaction product thereby allowing only a small part of the limestone to react. Where multiple stage beds are employed to overcome this difficulty, high pressure drops usually result across the apparatus with attendant high-energy requirements. Thus, the most common solution to the aforementioned problems is to provide an excess of limestone or dolomite to make up for the unreacted material.

Another disadvantage of known combustion techniques is the formation of nitrogen oxides in the flue gas. These oxides, which form nitric and nitrous acids upon combining with water, cause a major environmental hazard. The formation of nitrogen oxides results from the operation of combustors at relatively high temperatures. Even in the fluidized bed combustor operating at lower temperatures, some nitrogen oxides are produced. While multistage fluidized combustors are being tested in an attempt to reduce the formation of these impurities, as developed above, such combustors involve a high pressure drop across the apparatus with its attendant high-energy requirements.

With the increase in the diversity of materials which need to be burned, combustion apparatus and methods appear to becoming complex. For instance, several hundred billion pounds of refuse are being generated presently each year in the United States alone. The term "refuse" is a term of art which connotes a conglomeration of such diverse materials as cardboard, newspaper, plastic film, leather, molded plastics, rubber, garbage, fluid, stones and metallics, etc. as indicated, for example, in the American Paper Institute Report No. 114, Sept. 11, 1967. Other forms of particulate solids materials or solid-laden gases, sludges, or the like, resulting from municipal sewage sludge, spent foundry sand, refinery sludge, among other waste materials, require disposal. A method for such disposal is incineration. However, government regulations have become very stringent with respect to the types and concentrations of pollutants that may be discharged into our physical environment, virtually prohibiting incineration of waste by many of the heretofore commonly accepted techniques. Similarly, large amounts of convenient open space are no longer available for sanitary land fills and, in any event, communities can no longer tolerate contamination of streams and underground waters from such fills.

Prior art workers have addressed themselves to the problems associated with the combustion or incineration of the above mentioned diverse materials arising from industrial, residential and commercial sources. In addition, it has been an objective for many years to reclaim or recover heat from such waste materials for useful purposes. For example, prior processes have been directed to refuse disposal and heat recovery in steam boilers.

In view of the above brief overview of known methods and apparatus for combustion of materials and utilization of heat therefrom, it is evident that further improvements are needed.

SUMMARY OF THE INVENTION

This invention relates to a method and apparatus for combustion of diverse materials particularly combustible solids, gases or liquids, and mixtures thereof. The latter invention offers an economic and efficient method of carrying out the combustion of such particulate solid fuel compositions. Accordingly, organic or hydrocarbon-containing materials such as sewage sludge, coal, tar sands, coal shale, coal tailings, refinery sludge, municipal refuse, spent foundry sand, oily mill scale, among other types of incineratable materials, may be disposed of utilizing this invention. Furthermore, in accordance with the invention and its operating principles, heat may be recovered from such diverse combustible or waste materials for useful purposes, particularly for utilization in steam boilers, i.e., those employed in a utility power plant or industrial steam plant.

This invention provides a unique rotary combustion apparatus having mechanical means on its internal surface which, when rotated about its horizontal axis at a suitable speed, allows solids to become "mechanically fluidized" and to cascade down through a stream of combustion gas in the apparatus. The cascading action of the hot solids establishes intimate contact with the combustion gas or other gases formed in the combustion section in a manner somewhat analogous to the contact in a fluidized bed and, it may be said analogously that the solids become "mechanically fluidized". However, the necessity of fluidization by a high-velocity stream of gas is obviated as are the high-energy requirements associated with it. This invention also eliminates the need for expensive pulverizers, high pressure air handling systems, external pollution control devices and other complex or unreliable equipment. Many of the other disadvantages associated with the above-described systems of the prior art are eliminated according to the principles of this invention. Furthermore, this invention provides a method and apparatus for optimizing heat transfer, solids and gas contacting, and solids transport in combustion of solid materials. This invention also enables the combustion of a wide variety of diverse materials and the recovery of heat therefrom for useful purposes. These advantages and other advantages will become apparent in view of the detailed description which follows.

In one preferred form, the combustion apparatus of this invention comprises a rotary chamber, i.e., a cylindrical drum, or other similar regularly shaped chamber, suitable for rotation about a substantially horizontal axis. The combustion chamber has an inlet and an outlet whereby the combustible materials are introduced at the feed end and any residual solids may exit at the outlet end. The invention is particularly adaptable to fuels which have a high volatiles content and the apparatus provides zones of combustion thereby insuring that the volatiles be driven off and combusted in the gas stream, while allowing suitable residence time to insure complete combustion of the remaining char or carbonaceous residue. In this particular adaptation, at the feed end there is a short initial combustion zone, termed the "ignition zone", wherein the feedstock is quickly dried and brought up to ignition temperature by recirculating solids. Some volatiles may be driven off in this ignition zone. This is followed by a relatively constant temperature combustion zone, termed the "principal combustion zone", wherein additional volatiles are driven out of the feedstock and combusted in the hot gas stream and residual carbonaceous char also burns. The principal combustion zone is followed by a "falling temperature zone", wherein the final combustion of the char takes place and wherein sensible heat in the gases and solids may be used in steam generation. In this latter zone, the gases and solids are cooled before they enter a short disengaging section from which they leave the combustor separately at the outlet.

The method for combusting a feedstock of particulate combustible solids employing the rotary elongated combustion chamber above mentioned includes the following steps. The combustible particulate solids or particulate solids containing a combustible component are first introduced into the rotary elongated chamber which is adapted for rotation about a substantially horizontal axis. The chamber has an inlet and an outlet and, preferably, mechanical means on the inside surface of the chamber for lifting and cascading the combustible solids through a stream of combustion gas in the chamber. Additionally, there is a means for introducing an oxidizing gas into the chamber. The feedstock solids are subjected to combustion and heat may be recovered therefrom. When a solid combustible material such as coal is fed into one end of the chamber, as the chamber rotates the lifters attached to the inside surface cascade the coal material through the chamber and, at the same time, assist in propelling the combustible material through the combustion chamber for the removal of spent material or ash.

There are other further preferred features of the practice of the invention. Included in the apparatus is a means for recycling hot spent solids after combustion from a downstream end for mixing with the combustible solids of the combustion zone to the ignition end of the combustion zone. Distinct advantages are achieved by recycling hot solids, namely, the combustible feedstock is preheated, conditioned or it may be kept free-flowing in the case of sticky solids. For instance, this permits the combustion of so called "caking" coals, for example, which tend to form sticky masses during combustion. These sticky masses cause considerable difficulty in the conventional fluidized bed and other conventional methods of combustion.

In one practice of the method, combustion air introduction means is located near the inlet or feed end of the rotary combustion chamber where the particulate combustible solids are introduced. As indicated above, lifters are attached to the inside surface of the chamber to provide a means for lifting and cascading the combustible solids in the chamber and, by introducing air near the inlet of the combustion chamber, the combustion gases or burning fuel mixture establish an intimate contact of the cascading combustible solids with the gases in the combustor such that it may be said that the feedstock becomes mechanically fluidized as stated above. The means for lifting and cascading preferably comprises a plurality of lifters attached to the interior of the combustion chamber. Also, the inner surface of the chamber is lined with a refractory heat-resistant material. A combined solid cooler/air preheater section may be provided after the combustion section for heating ambient combustion air to provide the air for introduction into the combustion section and to cool solids simultaneously passing through the preheater section. The lifters attached to the interior of the combustion chamber stand into the chamber distance of up to about 1/40 to 1/10 the diameter of the combustion section. The solid materials are lifted by said lifting means in the combustion chamber while the chamber is rotating at a speed defined by the following empirical relationship:

$$\text{Revolutions per minute} = A \sqrt{\frac{3}{\text{inside diameter in feet}}}$$

in which A may have a value between about 10 and 40, with values of 15 to 25 preferred, such that gas is entrained by the cascading solid material resulting in mechanical fluidization.

The apparatus for recycling hot solids downstream from the inlet end of the combustion chamber comprise an open-ended, closed helical duct formed about an outer wall of the combustion chamber in a direction counter to its direction for rotation for picking up a portion of the solids from a point close to the outlet end of the combustion chamber and returning the solids to a point close to the inlet or ignition end of the chamber. Recirculation of the hot solids to the feed end as indicated above serves the purpose of rapidly bringing the cold combustible mixture up to the ignition temperature. The amount of recirculated material may be as high as 30 parts recirculated to 1 part of feed, or much smaller amount may be recirculated depending upon the characteristics of the coal or other combustible being combusted and upon the air preheat temperature. According to this invention, the circulation is thus accomplished in a considerably simpler more energy-efficient manner than in a conventional fluidized bed combustor which requires removal of the recirculated solids from the overhead gas stream and reinjection into the bottom of the fluidized bed which is at a considerably higher pressure.

In another preferred aspect of the invention, a heat transfer coil or bundle may be mounted inside a rotating chamber. The bundle may be similar to the so-called U-tube bundle found in conventional heat exchangers. Other arrangements may also be used such as a fixed tube sheet bundle with no shell. The tubes would have water flowing internally and their external surfaces are exposed to hot gases formed by combustion of the combustible solids throughout the rotary combustor. As the hot solids are cascaded by means of the lifters and are mechanically fluidized, they pass over the external surface of the water-filled tubes transferring additional heat and, at the same time, entrained hot gases also transfer a portion of their heat to the liquid inside the tubes. Moreover, the juxtaposition of the incandescent particles insures a high rate of radiant heat transfer as well as convection heat transfer. The combined heats from the hot gases and the cascading solids result in the heating and vaporization of the water inside the tubes resulting in the formation of steam, for example. On the other hand, as the solids and entrained gases pass over water-filled tubes, water may simply be heated rather than generating steam. In the alternative, hot gases may be used externally to the apparatus for steam manufacture or other purposes. In some cases, the temperature of the hot gases may be controlled by the addition of excess air quantities.

In a preferred form of the invention, an improved apparatus for carrying out the combustion of coal or other hydrocarbon-containing solid combustible material is provided which effectively eliminates disadvantages of the coal combustors of the prior art. Furthermore, an improved coal furnace for the purpose of generating steam is provided. In these embodiments, coal or other combustible is fed into one end of the rotating combustion chamber. As indicated above, the combustion chamber is equipped with internal lifters and, in some cases, recirculating chutes may be provided. The combustion chamber is rotated at a suitable speed to allow for the mechanical fluidization whereby the combustible coal solids cascade down through the flue gases formed by the combustion, or entraining gases during this operation. Where sulfur oxide gases may be formed during combustion of the coal fuel by oxidation of the sulfur, such gases may be simultaneously reacted during combustion with limestone or dolomite in the feedstock yielding a flue gas in which the sulfur oxides are greatly reduced, thereby making it very desirable from an environmental point of view. The nature of the "mechanical fluidization" produced by the cascading solids through the gas stream is such that the solid fuel mixture, for example coal and limestone or dolomite, does not have to be crushed to the same degree of uniform size as it does in the case of the conventional fluidized bed, thus eliminating the significant cost of relatively fine grinding and sizing the feed. In the preferred apparatus, all particle sizes are treated virtually the same as far as the combustion and reaction are concerned. Therefore, the method of handling the limestone or dolomite represents a distinct advantage over the fluidized method of combustion. As mentioned above, in the fluidized bed method, the limestone or dolomite must be of a size similar to the fuel in order to maintain these particles in the fluidized state. Thus, the limestone or dolomite must be relatively uniform and large in size to insure fluidization and to prevent it from being carried out with the flue gases. Such large-size particles also become coated with the sulfur oxide reaction products thereby preventing the unreacted core material from easily reacting. In the present invention, limestone or dolomite particles may be introduced in a finer state than the fuel, thus increasing their relative reactivity and increasing their exposed surface area. This results in a reduction in the limestone or dolomite requirements by comparison.

Thus, the apparatus and method of this invention provides for fully continuous and integrated processes where combustible particulate solids or solids containing a combustible component, may be burned and provide useful sources of heat. The particulate solids may have a range of sizes, limited only by the size and dimension of the apparatus for passage of the solids therethrough. The present invention also offers a very distinct advantage in that it enables the direct transfer of process heat. Hot recycled spent solids also provides heat as indicated above to either condition the incoming feedstock or to bring it up to ignition temperature.

Moreover, high rates of heat and mass transfer result in relatively small volume units that compare to conventional furnaces or furnace boilers. A highly efficient process is provided and additional recovery of heat from the flue gases indirectly may be achieved by heat exchange with the incoming air since a hot flue gas duct may also be constructed to traverse a solids cooler/air preheater section. Furthermore, as indicated above, the solids cooler/air preheater section may be employed enabling the solids to heat incoming combustion air. The hot flue gases may also be sent through a waste heat boiler for generation of process steam or to provide other heat recovery. Another advantage of the invention is that combustible solids or solids-sludge mixtures are prevented from agglomerating in the unit by recirculation of the spent solids which acts as a coating agent for sticky materials which may be formed or released in the combustion section, thus keeping such materials free-flowing. It will be appreciated, in view hereof, that the transport of solids through the unit is accomplished without high-energy requirements that are characteristic of other conventional systems.

Because of the staged combustion in the preferred operation of the rotary combustion apparatus, the temperature of the combustion may be controlled in the range of 1200° F. to 1600° F., for example, which in turn reduces the formation of nitrogen oxides. Also by reducing the ratio of actual to stoichiometric air, the nitrogen oxides may be reduced, resulting in total nitrogen oxide concentrations in the exhaust gases as low as 100 ppm. A further advantage of the instant invention is that gases undergo exceedingly low-pressure drop across the combustion chamber as compared to a fluidized bed combustor wherein the air must be sufficiently compressed to cause it to pass through a distributor and maintain sufficient velocity to fluidize the solids. The control of operating temperature may be affected in the combustion chamber by several means. For example, introduction of combustion air at different locations within the combustor may provide a shortage of air in the initial combustion zone with additional air being added at some point in the principal combustion zone. Furthermore, spent dolomite at its lower discharge temperature may be recirculated to the feed end resulting in temperature reduction at this point of the combustor. Turn-down of the operating capacity may be easily brought about. Simple reduction in the feed rate of combustible solids would quickly cut down the amount of hot gases and, therefore, the amount of steam manufactured. A limiting condition would be the point at which sufficient heat is removed by the tube bundle so that combustion is no longer supported. Another effective means of turning the capacity down would be to reduce the speed of rotation of the combustion chamber to the point that cascading of solids no longer occurs. At this point, the sliding solids would present a smaller exposed surface than when cascading and the combustor would be effectively banked. This would be a limiting condition and greater or lesser degrees of cascading can be employed successfully by adjusting the speed of rotation.

The combustible solids or solids containing combustible components which may be processed according to the method and apparatus of invention vary over wide classes of chemical constitution. Any solid which may be subjected to combustion may be employed. Furthermore, any combustible liquid, gas, mixtures of liquids and solids, and various combinations of such combustible materials, may also be employed providing that included in the combustible feedstock or recycle materials is a particulate solid material. A preferred class of combustible solids include hydrocarbon-containing minerals. Particularly included in this class are those materials selected from the group of bituminous or anthracite coal, coke, lignite, peat, combustible garbage, refuse, sewage or refinery sludge, coal shale, coal tailings, spent foundry sand, tar sands, oily mill scale, oil sand, wood, mixtures of these materials or other materials. As developed above, this invention is especially directed to the recovery of heat from such sources of organic or hydrocarbon-containing materials such as coal for use in a steam boiler. A further advantage of the present invention is that when employing such combustible solids such as coal having undesirable chemical constituents such as sulfur-containing compounds, such compounds are also capable of being removed from the combustible solids without undesirable environmental pollution. To achieve such results, limestone, dolomite or other absorbent, adsorbent or reactants are capable of removing such sulfur-containing compounds. This may be accomplished in a number of manners by operating, for example, at temperatures favorable to $SO_2$ sorption thereby eliminating an important environmental problem. Favorable operating temperatures in the combustion section are maintained between about 1200° F. and 1600° F. for such purpose. Furthermore, operating at such temperatures reduces the formation of nitrogen oxides as indicated above in the flue gases as well as providing efficient sorption of sulfur oxides by the limestone, dolomite or burnt lime components introduced with the particulate combustible materials. Particle size of the combustible solid materials may vary over a wide range from dusty fines to coarse lumps.

It will thus be understood that this invention provides a simple compact combustion apparatus having a heat transfer surface suitable for vaporization or heating of water or other liquid and wherein stabilized conditions of combustion occur at least in part in direct contact with the heat transfer surface. Furthermore, internal or external recirculation chutes are provided by this invention which permit recirculation of hot spent solids, for example, from the discharge end of the combustion zone to the inlet end of the ignition zone for the purpose of furnishing heat to the incoming solids. Thus this invention provides for efficient and controllable combustion over a 4 to 5-fold range of variation of the combustion range from minimum to maximum operating rates of the rotary combustor. The apparatus also provides for an accelerated heat transfer to internally distributed heat transfer surfaces by utilization of the radiation, convection and conduction modes of heat transfer from cascading incandescent solids in contact with the heat transfer surfaces. A mechanical fluidization of the solids in the combustion zone from the inlet end to the spent discharge end assures efficient conditions of combustion for the residual carbon in the combustible particulate solids, particularly in the recycle of such spent materials as in one of the preferred embodiments of this invention. This phenomenon might also be referred to as cascade turbulence throughout the combustion zone which intensifies and accelerates the combustion process, thereby assuring a compact and low-cost apparatus. It will therefore become evident that this invention provides a means of transferring solids through a rotary apparatus for combustion without consuming energy in the transfer except for the rotation of the rotary apparatus or drum itself without the necessity for complex external or internal transfer devices. Employing the apparatus of this invention, solids recycle chutes and ducts are an integral part of the assembly to assure economy in construction, erection and operation of the system. In this connection, an apparatus is provided in which the high rates of heat and mass transfer result in a very efficient use of volume, thus reducing the required size of the apparatus. This invention, its objectives and many advantages, may be further understood by reference to the following detailed description with reference to the accompanying figures.

BRIEF DESCRIPTION OF THE FIGURES

FIG. 1 is a side elevation in cross-section along the longitudinal axis of a rotary combustor of this invention by a plane perpendicular to the base with a combustor having an internal U-tube bundle which rotates with the combustor.

FIG. 2 is an end elevation in cross-section of FIG. 1 taken approximately through the mid-point of the rotating cylinder looking toward the feed end.

DETAILED DESCRIPTION

Figure 3:
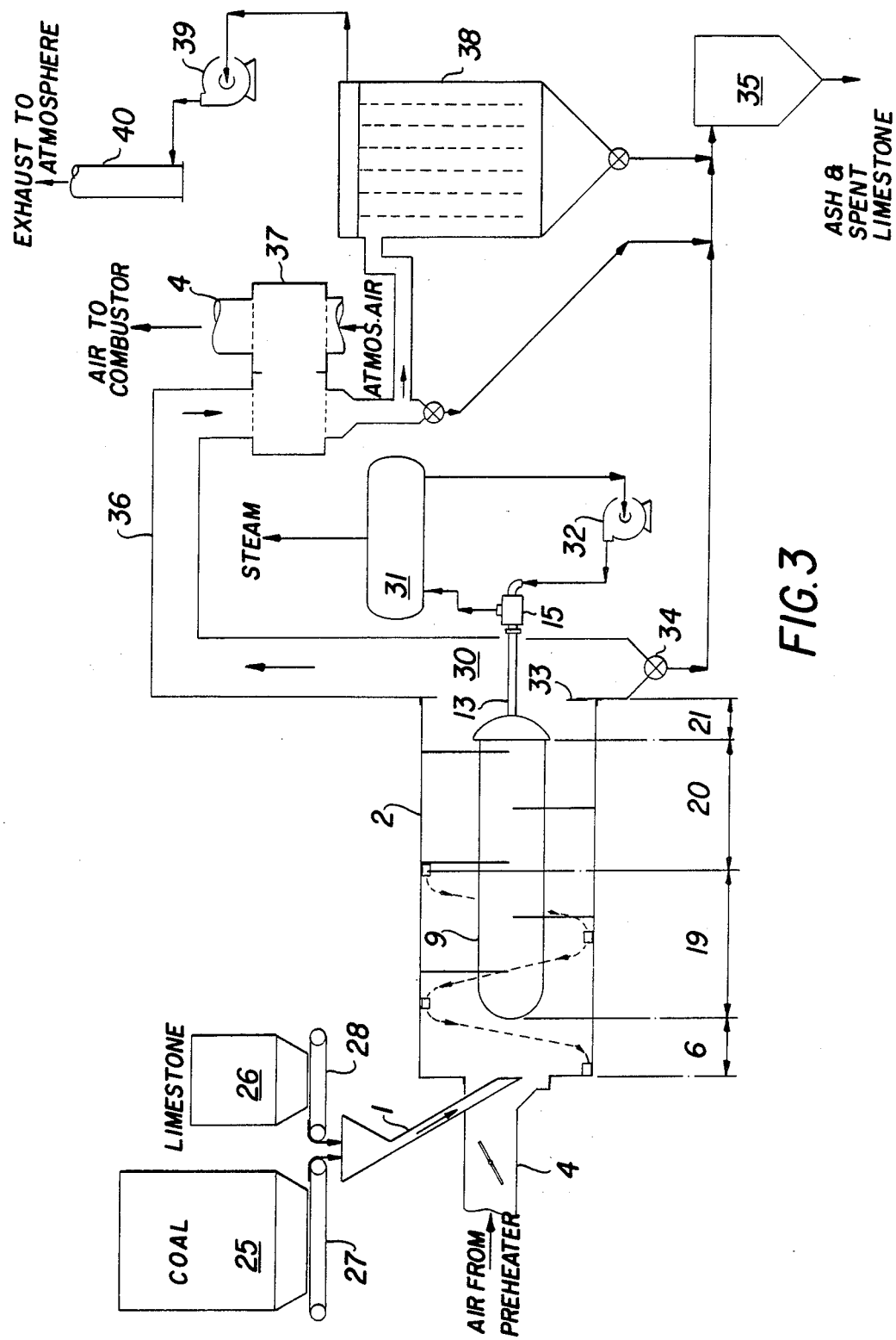
FIG. 3 is a typical flowsheet for a system using the present invention for the purpose of generating steam.

EXAMPLE I—Rotary Coal Fired Burner For Generating Steam

FIG. 1 depicts one example of a rotary combustion apparatus in accordance with the principles of this invention. The following description relates to the use of coal as the combustible solids, mixed with limestone or dolomite in a proportion related to the sulfur content of the combustible coal.

The combustion apparatus of FIG. 1 includes a cylindrical chamber 2 supported for rotation by cylindrical tires 3 and driven by a variable-speed drive in a conventional manner (not shown). Chamber 2 is lined with a refractory heat-resistant material 24 of a type suitable to withstand the maximum temperatures attained during combustion. Combustion air, usually preheated but not necessarily, is introduced at the feed or inlet end by means of a stationary duct 4 which is sealed into the cylinder feed end-plate by a simple, conventional rotating seal 5. The quantity of combustion air introduced is usually about 5 to 20% greater than the theoretical quantity required. Coal and limestone or dolomite in a proportion related to the sulfur content of the combustible solids are fed into the feed chute 1. The proportion, based upon the molar ratio of calcium to sulfur, may be within the range of 1:1 up to about 3:1 or higher, depending upon the amount of excess to be carried. An economical and practical proportion may be within the range of about 1.5 to 2.5:1. As the mixture of coal and limestone or dolomite falls into the inlet end of the rotating chamber 2, it passes into the ignition zone 6 where it is mixed with recycled hot solids by means of recycle chute 7 and lifted by lifters 8 which lift and cascade the mixed solids down through the gas stream which passes through the rotary combustion chamber 2. The rotational speed of the cylinder may be varied and, for a cylinder of about 11 feet inside diameter, the rotational speed according to the formula contained herein would be approximately 11 rpm. Sufficient hot recycle solids at a temperature of about 1400° F. to 1800° F. are introduced into ignition zone 6 to insure ignition of the combustible coal. Some volatile materials are driven from the feedstock in this zone. For a rotary combustion chamber having a 12 feet outside diameter and a length of about 38 feet 9 inches, the initial ignition zone might be about 5 feet long, for example.

A tube bundle 9 is mounted inside the rotating chamber 2 by means of tangential or other supports 10. This is best shown by FIGS. 1 and 2. In the arrangement shown in this example, 180 U-shaped loops of 2-inch tubes are shown with a total external area of approximately 5800 square feet. The 180 loops have 360 tube ends and the tubes are arranged in square pitch with 4-inch spacing. The tube bundle 9 consists of what is commonly referred to as U-tubes attached to the far end of the tube sheet 11. Thus, when steam is being manufactured or other liquid is being heated or vaporized, this arrangement insures good contact of the tubes with the cascading solids and ease of discharge of solids from the tube bundle. The tube sheet is attached to channel 12 from which projects the steam outlet pipe 13. Inside of the steam outlet pipe and concentric with it is the water feed pipe 14. In some cases this arrangement is reversed with the steam outlet pipe 13 on the inside and water feed pipe 14 on the outside. Both of these pipes are attached to a conventional rotary seal 15 which permits water feed and discharge of the steam without leakage. The water feed pipe 14 passes through a baffle 16 which separates the water feed channel of the U-tubes 17 from the discharge channel 18. In this manner, feed water is circulated through the inside of the U-tubes. Heat is transferred through the U-tubes by hot gases and cascading hot solids flowing over the tubes on the outside, thereby converting some of the circulating water inside the tubes to steam.

After the ignition zone 6, and starting at the end of the tube bundle 9, is the principal combustion zone 19 wherein the temperature of the gases and solids are maintained at about 1200° F. to about 1600° F., depending upon the nature of the combustible feedstock. In this zone, additional volatile materials from the coal or other feedstock and the carbonaceous residue or char are combusted. In the combustion zone, lifters 8 are provided to lift and cascade the hot combustible material mixed with limestone or dolomite through the hot gases and over and between the U-tubes of the tube bundle 9. A typical length for the principal combustion zone of this example, with a cylinder outside diameter of 12 feet, is about 13 feet 6 inches. From the principal combustion zone 19, the hot gases and hot solids proceed to the falling temperature combustion zone 20 wherein the gases and hot solids are cooled from the temperature of combustion to about 700° F. to 1200° F. The falling temperature combustion zone also serves to complete the combustion of the char or carbonaceous residue. This zone extends to the end of the heat transfer surface of tube bundle 9 and is equipped with lifters 8 which cascade the solids through the stream of gases and over and between the U-tubes of the tube bundle 9. For this example, a typical length of the falling temperature combustion zone is about 20 feet 3 inches. The final zone is the disengaging zone 21 containing no lifters wherein solids are allowed to separate from the gas stream. The solids at the point of discharge are essentially ash mixed with spent limestone or dolomite. In the present example, a typical disengaging zone length of about 3 feet 9 inches is provided. The solids pass over discharge weir plate 33 into a breach section and thence into stationary chute 22 for ash disposal. Gases are sent to an air preheater and/or a dust collector via the stationary breach section 30, which is sealed with respect to the discharge end plate by a simple conventional rotary seal arrangement 23. In operation, as the coal fired burner is employed for the production of steam, throughout the length of the rotary combustor, sulfur oxides formed during combustion react with previously unreacted and/or recirculated limestone or dolomite. Typically over 95% of the sulfur oxides enter the gas stream and the remainder reside with the ash. The amount of sulfur oxides remaining with the ash varies significantly with the alkali content of the coal. In any event, the sulfur oxides residing with the ash are in stable chemical combination. The sulfur trioxides, which constitutes about 1% or less of the total sulfur oxides in the gas stream, react with limestone or dolomite to form calcium sulfate. The sulfur dioxide reacts with limestone or dolomite to form calcium sulfite. These sulfites are essentially oxidized in the presence of excess air at the operating temperatures to calcium sulfate. By this means, the sulfur oxides are effectively removed from the exhaust gases. Typically, 90% of the total sulfur oxides in the gas stream are removed by the dolomite or limestone.

With reference to FIG. 3, a flowsheet is depicted for a system using the present invention to manufacture 250 psig steam employing coal as the fuel with an apparatus similar to that shown in FIG. 1. Coal containing about 2.5 weight percent sulfur from a storage bin 25 is mixed with limestone supplied from storage bin 26 by conveyor belts 27 and 28, respectively, into the feed chute 1. About 2100 pounds of coal and about 200-240 pounds of limestone are introduced per hour through feed chute 1 into the inlet or feed end of the rotary chamber 2 which has, in this example, an outside diameter of about 9 feet 6 inches and an inside diameter of about 8 feet with an overall length of about 38 feet 6 inches and which is rotated at about 8 to 14 rpm. Preheated air at about 600° F. from a Ljungstrom-type regenerative air preheater 37 shown downstream at a volume of 5240 standard cubic feet per minute is also fed into this rotary boiler through air duct 4. In the initial ignition zone 6 of the rotary chamber 2, the fuel is mixed with hot, internally recycled solids at about 1500° F. sufficient in quantity to dry the fuel and bring it up to the ignition temperature. The ignited fuel, limestone and recycled solids then progress to a relatively constant temperature combustion zone (termed the principal combustion zone) 19 having a temperature of about 1300° F. to 1600° F., where the solids are lifted and cascaded down through the hot gas stream over and between the tube bank or bundle 9, transferring heat along with the hot gases to 40 gallons per minute of make-up boiler feed water circulated through the inside of the tubes. Most of the combustion occurs in this zone and some of the feed water is converted to steam. The hot combustion gases and hot solids then pass into the falling temperature combustion zone 20 where the solids continue to be lifted and cascaded through the hot gas stream and over and between the tubes of the tube bundle 9. Some final combustion occurs in this zone and sensible heat in the gases and solids is utilized to generate steam. In this zone, the gases and solids are cooled to about 800° F. before entering the disengaging zone 21 with no lifters, located at the discharge end of the rotary chamber past the point at which the tubes terminate in the tube bank. In this zone, the solids and gases separate from one another and pass into the breach section of the unit 30. The solids which separate from the gases in the disengaging zone 21 pass over an adjustable weir plate 33 into the breach section 30 and thence through a rotary star valve 34 for conveyance pneumatically to an ash silo 35. A typical quantity of ash and spent limestone discharge from the rotary boiler would be 450 to 490 pounds per hour at 800° F. In this Example, about 25,600 pounds per hour of gases at 800° F. leave the rotary combustor. These gases flow through a discharge duct 36 to a regenerative air preheater 37. In this preheater, 23,600 pounds per hour of atmospheric air at 70° F., with a volume of 5240 standard cubic feet per minute, are heated to 600° F. while cooling the gas stream from the rotary boiler to 275° to 300° F. The cooled gas stream from the air preheater 37 is sent to a conventional bag filter 38 and thence through a conventional induced-draft (ID) fan 39 to a stack 40 for discharge to the atmosphere.

The mixture of water and steam generated in the tube bundle 9 passes through discharge pipe 13 through rotary seal 15 into steam drum 31 where feed water and steam are separated. Separated water from the steam drum goes to the suction side of a recirculation pump 32 at which point it combines with 40 gpm of fresh boiler feed water which has been deaerated. Feed water enters the tube bundle through a pipe which is concentric with discharge pipe 13. Employing the amounts of coal and limestone aforementioned having a −16 U.S. sieve size, and when feeding 23,600 pounds per hour of air at 70° F., 20,000 pounds per hour of steam will be generated at 250 psig and 406° F. when 40 gpm of deaerated boiler feed water is fed to the system at 70° F. Under the above conditions, 450 to 490 pounds per hour of ash plus spent limestone would be discharged such that the overall sulfur removal efficiency would be about 80-90% by weight. When discharging flue gases to the atmosphere at 275°-300° F., the overall boiler thermal efficiency would be 85-90%, based upon the higher heating value of the fuel.

While FIGS. 1–3 depict a specific type combustor having hot gases utilized in the combustor for heat exchange with steam generating tubes, other types of combustors are contemplated by the present invention as it should be understood to a person of ordinary skill in view of this description. For instance, combustor may be employed where the heat is not transferred within the combustor, rather the hot gases formed by the combustion are conducted out of the combustor to be used elsewhere. In this type of combustor, the apparatus of FIG. 1 may be modified to exclude the tube bundle 9 and conditions of operation of the rotary combustor are essentially the same except that in this arrangement where there is no tube bundle, there is no falling temperature zone. The solids pass into a short disengaging section where the solids and gases are separate from one another and the hot gases continue out of the rotary combustor through a hot gas duct. The hot gases may then be taken to a boiler for the purpose of making steam, or to another form of heat exchanger to heat or vaporize water or other liquid, or to dry solids such as coal or other material or to any other apparatus which permits the transfer of heat from a gas stream at an inlet temperature of about 1400° F. to about 2800° F. In other variations of the apparatus described in connection with FIGS. 1–3, the U-bundle 9 may be stationary and thus does not rotate with the rotating cylinder. This may be accomplished by attaching the U-tube bundle to a stationary pedestal. Of course, a stationary tube bundle may be of the fixed tube-sheet type instead of the U-tube type. Such an arrangement permits support at both ends for a condition where the U-tube bundle would be so long as to make cantilevering impractical. Furthermore, if the partitioning of the tube-sheet channels is such that entry of the water and discharge of steam are at different ends, the bundle can be arranged to operate in either cocurrent or countercurrent flow with respect to the gases and solids in the rotating cylinder. Thus, it will be understood that for the purpose of generating steam, variations of the combustor and boiler arrangements may be made and may be of any conventional type. In addition to such variations to obtain efficient heat exchange from stationary or rotating tube bundles as above described, other means may also be provided to remove the hot gases from the combustion chamber to some other type of heat utilization device.

EXAMPLE II—Rotary Incinerator for Mill Scale Deoiling

Figure 4:
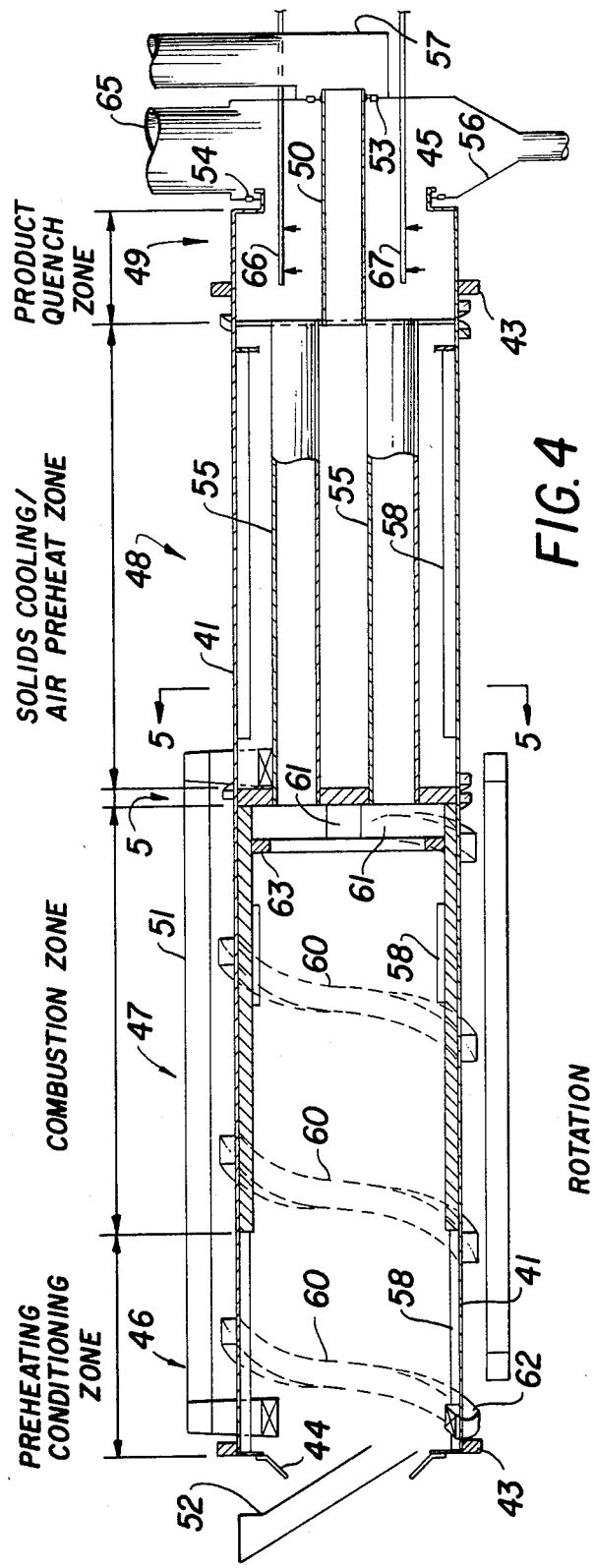
FIG. 4 is a side elevation in cross-section along the longitudinal axis of another rotary combustor of this invention by a plane perpendicular to the base with a combustor where the combustion air is designed to travel in a countercurrent manner with respect to combustible solids in the combustion zone. This apparatus as shown may be employed as a rotary mill scale reactor or incinerator. Further, with minor modification, it may be employed as a foundry sand incinerator or refinery sludge incinerator.

FIG. 4 depicts another example of a rotary combustion apparatus in accordance with the principles of this invention. The following description relates to the use of oily mill scale as a feedstock for the apparatus and the rotary incinerator has been designed to meet the needs of the steel industry for deoiling mill scale and mill scale sludge.

Figure 5:
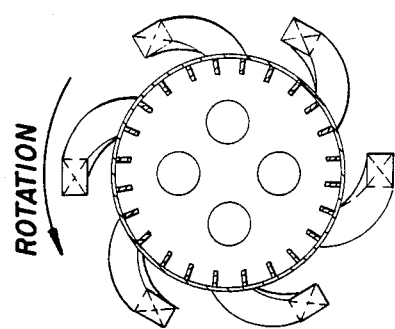
FIG. 5 is an end elevation of FIG. 4 in cross-section taken approximately through the mid-point of the cylinder looking toward the discharge end.

The rotary combustion apparatus of FIG. 4 includes a cylindrical chamber 41 supported by drum tires 43 and equipped with a conventional variable-speed driving means. The chamber 41 is provided with a particulate solids feed opening 44 and discharge outlet 45. The chamber 41 is divided into a preheating/conditioning zone 46, a combustion zone 47 and a solids cooling/air preheat zone 48, and a product quench zone 49. Chute 52 delivers the oil containing mill scale and, if necessary, other solid materials into the apparatus. A rotating seal 54 seals opening 45 at stationary flue gas stack 65. Another seal 53 seals the cool air duct 50 at the opening to stationary air duct 57. These seals are of conventional type. Deoiled mill scale is discharged through chute 56. The rotary combustion apparatus 41 is lined with a refractory heat-resistant material of the type suitable to withstand the maximum combustion temperatures therein. The recirculation means consisting of at least one helical chute 60 is mounted along the outside wall of chamber 41 and is open-ended at its inlet end 61 and outlet end 62. The helical chute curves around chamber 41 in a direction counter to the direction of rotation so that material entering inlet 61 is carried back toward the feed opening 44 until it is discharged into the chamber through outlet 62. Lifters 58 are attached to the interior wall of the combustion chamber in the preheating/conditioning, combustion and solids cooling/air preheat zones. The lifters 58 project perpendicularly from interior wall of the rotary combustion apparatus. The lifters 58 are oriented parallel to the axis of rotation. There are no lifters for a short distance at the inlet and discharge of the solids cooler/air preheat zone 48. Lifters extend only for a short length in the third quarter of the combustion zone. There are no lifters in the product quench zone. FIG. 5 depicts a view of FIG. 4 through the chamber 31 looking toward the feed end. This cross-section is taken approximately through the front end of the solids cooling/air preheat zone 48 and shows the preheated air ducts 51 and exhaust ducts 55.

The principles of operation of the rotary incinerator of FIG. 4 are most flexible and will fully utilize whatever oil is present in the mill scale feed for combustion within the combustion zone of the rotary incinerator and no after burner is required. Any additional fuel needed can be added as oil or gas, however, and the rotary incinerator will process mill scale sludge as readily as regular oily mill scale. Thus, fuel costs will be minimized and the iron units in mill scale sludge will be recovered. The ambient wet feed is delivered to the rotary incinerator 41, particularly the preheating/conditioning zone where the feed is dried and preheated to about 800° F. by mixing the feed with up to 5 times as much hot recycle deoiled mill scale and by contact with the combustion air preheated to about 950° F. which enters the apparatus through air duct 51. The inlet air enters the apparatus and travels through cool air ducts 50, thence through solids cooler/air preheat zone 48, and thence through air duct 51 which extends to the front end of the combustion zone so that air with the highest oxygen content comes in contact with the mill scale entering the combustion zone with the recycled or spent mill scale. As the air moves cocurrently with respect to the solids it is intimately contacted by solids which cascade down through it and are, as previously described, mechanically fluidized and, in so doing, any residual oil or carbon in the mill scale is burned out until the resulting flue gases reach the entry opening of the exhaust ducts 55 and ultimately flue gas exhaust flue 65 through which they leave the apparatus. The deoiled mill scale leaves the apparatus through discharge chute 56. During the course of combustion the feed and recycled mill scale are cascaded by lifters in the preheat/conditioning zone to facilitate mixing and to serve as a screen to absorb the radiation from the combustion zone. Oil that is vaporized from the mill scale and mixed with preheated air is ignited by radiation at the entrance of the combustion zone. Where some auxiliary fuel is needed, temperature control in the combustion zone is achieved by controlling the amount of fuel added. Either gas or oil can serve as an auxiliary fuel. The auxiliary fuel is introduced at a point in the preheat/conditioning zone which will induce combustion at the beginning of the combustion zone.

For the first 9 feet of the combustion zone 47, solids are not cascaded to thereby allow the combustion temperature of the oil and fuel vapors in the gas phase to reach the 2000° F.+ level. Solids then travel through this zone by the normal rolling rotary action described above in connection with FIG. 1 and the amount of volume required for combustion is minimized. Toward the end of the combustion zone, a 4-foot long section of lifters is included to insure that the solids reach the required temperature and to cool the combustion gases to 1500° F. for fuel conservation. In connection with this example, it has been assumed that the solids are raised to about 1000° F. Following the combustion zone there is a 4-foot solids disengaging zone. At the end of the combustion zone 47, the hot solids pass over a dam ring 63 and into a splitter box 64 which recycles part of the hot solids through chute 60 to the feed end of the rotary apparatus and sends the rest through a transfer chute into the product or solids cooling/air preheat zone 48. In the first 2½ feet of the solids preheat zone 48, there are no lifters 58 to allow preheated air to be separated from the solids and pass through ducts 51 to the feed end of the preheating/conditioning zone 46. Lifters 58 are present in the next 16½ feet to insure good heat transfer from the hot solids to the air. Under design conditions, the air will be heated to 945° F. and the solids cooled to 555° F. One or more exhaust ducts 55 traverse this zone 48. At the end of this zone, the solids are transferred through a transfer chute into the product quenching zone 49. In the product quenching zone 49, exhaust gas at 1500° F. and dry deoiled mill scale at about 555° F. enter the zone. Since there are no lifters in this section, the gas and solids are not in good contact and they can be quenched individually. Stationary water sprays 66, mounted on pipes at a high level, quench the exhaust gas from 1500° F. to below 300° F. Water sprays 67 at a lower level are directed toward the rolling mill scale and cool it from 555° F. to about 200° F. The cooled solids pour out of the end of the rotary unit into product chute 46 and are directed out of the apparatus. Flue gases leave the apparatus through exhaust flue 65.

EXAMPLE III—Refinery Sludge Incineration

Figure 6:
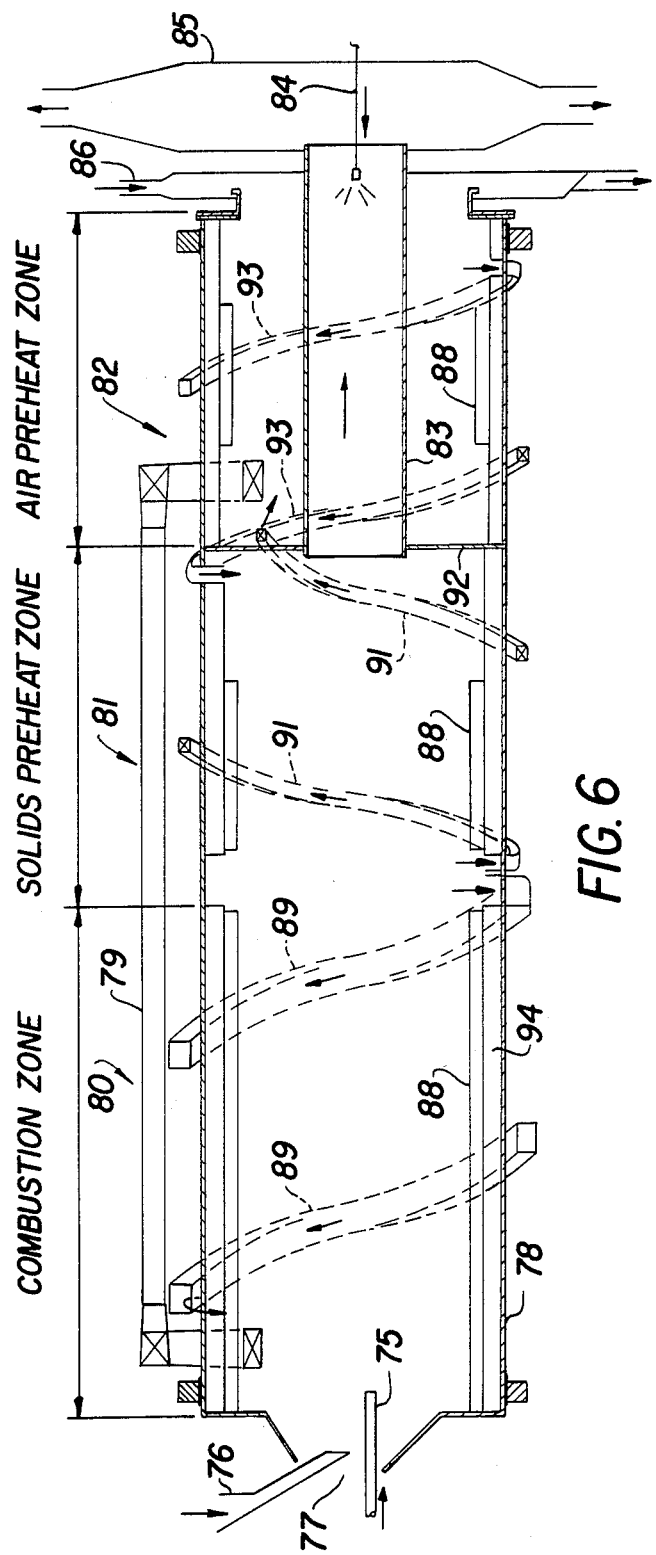
FIG. 6 is a side elevation in cross-section along the longitudinal axis of another incinerator apparatus similar to that of FIG. 4 but with some modifications.

Employing an incinerator apparatus somewhat similar to that described in connection with FIG. 4, but with some modifications, this invention may be utilized for incinerating refinery sludge. Such a rotary incinerator may be specifically designed for refinery sludge which can incinerate the sludge at about 2000° F. using coal to supply the additional heat required. When refinery sludge containing 5% oil, 10% solids, 85% water is incinerated, as assumed in this example for a design basis, only enough coal to supply 1650 Btu per pound of sludge is required. This amounts to about 12.5% by weight of the sludge. A high thermal efficiency is possible with the rotary incinerator because of its ability to recover heat from the exhaust gas. In this Example, an incinerator of the type shown in FIG. 6 is employed. The refinery sludge is fed through a pipe 75 and coal is introduced through a chute 76 into the inlet end 77 of the rotary incinerator 78. There the sludge and coal are mixed with hot recycled sand which dries the sludge and heats both the water vapor and dried solids to about 1200° F. Preheated air is also introduced into the front or inlet end of the incinerator through preheated air ducts 79 and burning takes place at temperatures of about 1200° F. to about 2000° F. Enough space is provided in the combustion zone 80 to provide 2-second residence time at about 2000° F. The cascading of the hot solids in the combustion zone 80 as hereinabove described in connection with the other examples insures complete combustion of the sludge. At the end of the combustion zone 80, heat is recovered from the hot combustion gases by passing them countercurrent to cascading solids in the solids reheat zone. After being cooled to about 1210° F., the combustion gases exit through an exhaust duct 83 running through the air preheat zone 82. Water sprays 84 cool the exhaust gas to about 300° F. before it passes through exhaust flue 85 and thence to a bag house and an ID fan (not shown). Air enters the air preheat zone 82 of the incinerator through air duct 86, and moves countercurrent to cascading hot solids from the solids reheat zone 81. Preheated air at about 1600° F. is conducted to the front end of the incinerator through preheated air ducts 79. Pressure drop through the incinerator is quite low, on the order of about 1 or 2-inch WC. By adjusting the draft from the ID fan, the pressure at the front end of the incinerator is maintained slightly below atmospheric pressure. Thus, the front of the incinerator can remain open for easy feeding, inspection and temperature measurement. Make up heat transfer solids, such as sand, are added at the front end of the incinerator. The fine portion of the residue or ash from the refinery sludge will exit with the combustion gas through exhaust flue 85 and can be captured in a bag house (not shown). Any coarse residue can serve as a heat transfer solid until it is discharged at the end of the air preheat zone of the rotary incinerator.

As stated above, the incinerator which may be employed in this example is a rotary unit of the type contemplated by this invention. Basically, it is a cylindrical unit having an outer diameter of about 12 feet 6 inches and is about 60 feet long. The combustion zone 80 is lined with a castable refractory 87 which is shaped to form lifters 88 and is approximately 25 feet in length. As with the apparatus described in the previous examples, a spiral chute 89 recycles heat transfer solids from the end of the combustion zone 80 to the front of the combustion zone to bring the feed up to ignition temperature. Following the combustion zone, and before the air preheat zone 82, there is a solids reheat zone 81 with lifters 88 of about 8 feet in length and a disengaging zone without lifters of about b 8 feet in length. A spiral chute 91 may be employed to conduct the hot solids from the front of the solids reheat zone 81 to the air preheat zone 82. This spiral chute is fashioned so that it is rotating with the axis of rotation of the rotary unit so that the solids may be transferred to the air preheat zone. Likewise, a spiral chute 93 may be employed to conduct solids from the discharage end of the air preheat zone 82 into the downstream end of the solids reheat zone 81. Combustion gas which is cooled to about 1210° F. passes into a 4-foot diameter exhaust duct 83 in the center of the air preheat section 82. The combustion gases are cooled to about 300° F. by water sprays 84 within the ducting before entering through exhaust flue 85 and thence to the bag house (not shown). The air preheat zone is separated from the solids preheat zone by a bulk head 92. Ducts for the preheated air 79 extend from the bulk head 92 to the front of the combustion zone 80. The air preheat zone is lined with refractory and is about an 8-foot section containing lifters. Complete combustion is achieved within the incinerator and no after burner is required.

EXAMPLE IV—Spent Foundry Sand Incineration

In this example, an incinerator similar to that described in connection with FIGS. 4 and 5 above is employed consisting essentially of four zones, namely, the feed preheating/conditioning zone, combustion zone, solids cooling/air preheat zone and product quench zone. Spent foundry sand may be contaminated with organic binders which cause it to be classified as a hazardous material. If the organics are burned out and metallic particles recovered by screening, the spent sand can be rendered nontoxic and may have a positive value as a land fill cover or similar use. Employing the method and rotary incinerator apparatus of this invention, the organic materials may be burned within the rotary apparatus and an after burner is not required. Minimum auxiliary fuel may be required because much of the sensible heat in the incinerated sand is recovered by preheating the combustion air.

For purposes of this example, a rotary incinerator is provided having a design similar to that described in FIGS. 4–5 above. The unit is essentially a drum having an overall length of about 23-feet 6-inches and an inside diameter of about 5-feet. In this case the drum consists of three individual compartments separated by dividing walls, i.e., a feed preheat and combustion compartment, product cooler compartment and a quench compartment. In the preheating/conditioning section, the fresh feed is mixed with recycle sand heated to about 1300° F. This dries the feed and preheats it to about 700° F. and the solids are then cascaded in this preheat section to provide a screen to minimize loss by radiation from the front of the incinerator. In the preheating/conditioning zone, preheated air from the solids cooling/air preheat zone is introduced by external ducts and a flame is developed as the decomposition products from the organic binders in the sand, and in the auxiliary fuel, which is added at the front end of the incinerator, are burned. In a 3-foot section at the front of the combustion zone, the cascading of sand is suppressed by shortening the lifters to allow for flame development and a high combustion rate. Following is a 6-foot 8-inch long cascading section to heat the sand to 1300° F. and to cool the combustion gases to about 1500° F. At the end of the combustion section there is a disengaging section and a dam ring which maintains the sand in the first compartment at the appropriate level. The hot sand that passes over the ring goes into a splitter box which recycles a portion to the front end of the incinerator and transfers the rest into the solids cooling air preheat zone. The combustion gases at about 1500° F. exit through four flues leading to the product quench zone. In solids cooling/air preheat zone the product is cooled from 1300° F. to about 700° F. by cascading it through the incoming air. This preheats the air from ambient conditions to about 1200° F. At the end of this compartment the sand passes over a dam ring which maintains the proper loading and then into a spiral chute which transfers the sand to the product quench zone. In the product quench zone, there is a set of stationary water sprays near the top of the compartment to cool the exhaust gases to about 250° F. in a manner similar to that described above in connection with the mill scale deoiling example. Another set of stationary water sprays is directed onto the sand to cool it from about 700° F. to about 210° F. after which the sand flows into a product recovery area in a manner similar to that described above.

Although the rotating chambers described herein are cylindrical, the principles of this invention do not require any specific shape and will, in fact, operate satisfactorily with any chamber having a regularly shaped cross-section area as, for example, a regular prism or a slender cone. In the latter case, the base of the cone might be at the discharge end of the combustion section for example, for cocurrent air flow in that section. This would provide a means for controlling the relative gas velocity by controlling the cross-sectional area. In this manner, the enlarged cross-section would result in a decreased gas velocity leading to greater settling of any entrained solids from the gas stream.

Having described the details of this invention, it is evident that it provides an arrangement and method for the combustion of combustible particulate solids or particulate solids containing a combustible component with certain advantages not heretofore attained in conventional arrangements. Although the description contained herein has been made with respect to relatively specific embodiments, it will become apparent to those of ordinary skill in this art that variations may be made and such are intended to be included without departing from the scope of this invention.

What is claimed is:

1. A method for combustion comprising
introducing particulate solids having a combustible component into a rotary elongated combustion chamber for rotation about a substantially horizontal axis having an inlet and an outlet,
introducing an oxidizing gas into said chamber for combustion of said combustible component,
passing a stream of combustion gas through said chamber,
rotating said chamber about its horizontal axis at a speed defined by the following empirical relationship:

$$\text{Revolutions per minute} = A \sqrt{\frac{3}{\text{inside diameter in feet}}}$$

in which A has a value between about 10 and 40, and
lifting and cascading said solids in said chamber through said stream of combustion gas resulting from said speed of rotation thereby achieving a mechanical fluidization of said solids in said combustion gas during combustion.

2. The method of claim 1 comprising recycling hot solids for mixing with said combustible solids.

3. The method of claim 1 comprising introducing the oxidizing gas at the inlet end of said chamber.

4. The method of claim 1 wherein said chamber interior provides an ignition zone, a combustion zone and a combined solids cooler/air preheater zone in series for the combustion of said solids and ambient combustion air is passed through said preheater zone prior to introduction into said combustion zone.

5. The method of claim 4 comprising recycling a portion of the hot solids from a downstream end of said combustion chamber to the inlet end of said chamber,
transferring the remaining hot solids to a front end of said combined solids cooler/air preheater zone,
introducing ambient combustion air into a discharge end of said solids cooler/air preheater zone,
cooling said solids by a countercurrent flow of combustion air while simultaneously preheating said combustion air,
transferring said preheated combustion air to an upstream end of said ignition zone, and
removing said solids from a discharge end of said solids cooler/air preheater zone.

6. The method of claim 1 further comprising utilization of the heat of said combustion.

7. The method of claim 1 further comprising utilization of the heat of said combustion for steam generation.

8. The method of claim 1 wherein said solids contain a combustible component selected from the group consisting of a solid, liquid, gas, and mixtures thereof.

9. The method of claim 8 wherein said solids contain a sulfur-containing compound and a material is added to said solids for the removal of the combustion products of said sulfur-containing compound.

10. The method of claim 1 wherein said combustible solids are selected from the group consisting of coal, coke, lignite, peat, combustible garbage, refuse, sewage sludge, refinery sludge, coal shale, coal tailings, oily mill scale, spent foundry sand, tar sands, oil sand, wood, and mixtures thereof.

11. The method of claim 21. wherein said solids comprise a hydrocarbon-containing material containing a sulfur-containing material and comprising the further step of adding a compound from the group consisting of limestone, dolomite, burnt lime, and mixtures thereof for the removal of said sulfur-containing material.

12. The method of claim 11 wherein said hydrocarbon-containing material is coal.

13. The method of claim 12 wherein the temperature of combustion in said chamber is maintained in the temperature range of about 1300° F. to about 1600° F.

14. The method of claim 1 wherein a pressure drop measured between a gas inlet and outlet for said chamber is in the range of about 0.01–0.02 inch of water column per foot of chamber length.

15. The method of claim 1 wherein said solids comprise a mixture of particle sizes limited only by the means to accommodate transfer of solids through said apparatus.

16. The method of claim 1 wherein said chamber includes as plurality of heat exchange tubes disposed within said chamber for carrying heat exchange fluid therethrough, said heat exchange tubes positioned such that said solids cascade around said heat exchange tubes as said chamber rotates.

17. A method for combustion comprising
introducing particulate solids having a combustible component into a rotary elongated combustion chamber for rotation about a substantially horizontal axis having an inlet and an outlet, said chamber having an ignition zone, a combustion zone and a falling temperature zone in series,
introducing an oxidizing gas into said chamber for combustion of said combustible component,
passing a stream of combustion gas through said chamber,
rotating said chamber about its horizontal axis at a speed defined by the following empirical relationship:

$$\text{Revolutions per minute} = A \sqrt{\frac{3}{\text{inside diameter in feet}}}$$

in which A has a value between about 10 and 40, and
lifting and cascading said solids in said chamber through said stream of combustion gas resulting from said speed of rotation thereby achieving a mechanical fluidization of said solids in said combustion gas during combustion,
igniting and combusting said solids in said chamber, and
recovery of the heat of combustion for utilization.

18. The method of claim 17 wherein said heat is recovered to generate steam.

19. The method of claim 18 wherein said solids comprise a sulfur-containing coal.

20. The method of claim 19 wherein an additive for the removal of sulfur from said coal is mixed with said solids.

21. The method of claim 20 wherein said additive is selected from the group consisting of limestone, dolomite, burnt lime and mixtures thereof.

22. A method for combustion comprising
introducing particulate solids having a combustible component into a rotary elongated combustion chamber for rotation about a substantially horizontal axis having an inlet and an outlet,
introducing an oxiding gas into said chamber for combustion of said combustible component,
passing a stream of combustion gas through said chamber,
rotating said chamber about its horizontal axis at a speed defined by the following empirical relationship:

$$\text{Revolutions per minute} = A \sqrt{\frac{3}{\text{inside diameter in feet}}}$$

in which A has a value between about 15 and 25, and
lifting and cascading said solids in said chamber through said stream of combustion gas resulting from said speed of rotation thereby achieving a mechanical fluidization of said solids in said combustion gas during combustion.

23. The method of claim 22 comprising
recycling hot solids for mixing with said combustible solids.

24. The method of claim 22 comprising recycling a portion of the hot solids from a downstream end of said combustion chamber to the inlet end of said chamber,
transferring the remaining hot solids to a front end of said combined solids cooler/air preheater zone,
introudcing ambient combustion air into a discharge end of said solids cooler/air preheater zone,
cooling said solids by a countercurrent flow of combustion air while simultaneously preheating said combustion air,
transferring said preheated combustion air to an upstream end of said ignition zone, and
removing said solids from a discharge end of said solids cooler/air preheater zone.

* * * * *

UNITED STATES PATENT AND TRADEMARK OFFICE
CERTIFICATE OF CORRECTION

PATENT NO.   :   4,583,468
DATED        :   April 22, 1986
INVENTOR(S)  :   Leland M. Reed et al It is certified that error appears in the above-identified patent and that said Letters Patent is hereby corrected as shown below:

Col. 15, line 10, "solids preheat zone" should be --solids cooling/air preheat zone--

Col. 16, line 37, "about b 8" should be --about 8--

Col. 19, line 14, "21" should be --1--

Signed and Sealed this

Twenty-fifth Day of November, 1986

*Attest:*

DONALD J. QUIGG

*Attesting Officer*        *Commissioner of Patents and Trademarks*